United States Patent [19]

Nagai et al.

[11] Patent Number: 4,963,653
[45] Date of Patent: Oct. 16, 1990

[54] SIALIC ACID-BONDED OCTAPEPTIDE AND PREPARATION THEREOF

[75] Inventors: Yoshitaka Nagai, Tokyo; Shohei Shibayama, Tokorozawa; Masaaki Numata, Kawagoe; Shoji Yoshimura, Iruma; Makoto Tanaka, Koshigaya; Masayoshi Ito, Kunitachi; Akira Awaya, Yokohama; Hisashi Kobayashi; Hayao Abe, both of Mobara; Yusaku Ishizuka, Yokohama; Tomoya Ogawa, Musashino, all of Japan

[73] Assignees: Mect Corporation; Mitsui Toatsu Chemical, Inc., both of Tokyo, Japan

[21] Appl. No.: 372,708

[22] Filed: Jun. 28, 1989

[30] Foreign Application Priority Data

Jun. 28, 1988 [JP] Japan .................. 63-159947

[51] Int. Cl.$^5$ .................. C07K 7/06; C07K 9/00
[52] U.S. Cl. .................. 530/322; 530/328; 530/333; 530/335; 530/337; 530/343
[58] Field of Search .............. 530/322, 328, 333, 335, 530/337, 343

[56] References Cited

U.S. PATENT DOCUMENTS 4,694,076  9/1987  Ogawa et al. .................. 536/18.6
4,797,477  1/1989  Yoshimura et al. .............. 536/18.7

Primary Examiner—Lester L. Lee
Attorney, Agent, or Firm—Oblon, Spivak, McClelland, Maier & Neustadt

[57] ABSTRACT

A sialic acid-bonded octapeptide represented by the following general formula (I):

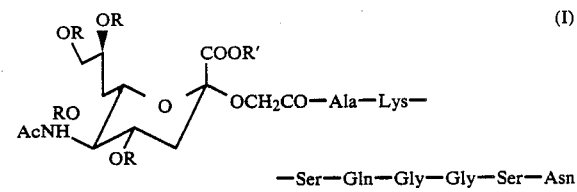

wherein R represents a hydrogen atom or an acetyl group; and R' represents a lower alkyl group, an aralkyl group, a hydrogen atom or an alkali metal atom, is herein disclosed. The peptide chain of the sialic acid-bonded octapeptide is constituted by 8 amino acid molecules on the C-terminus side of FTS and the compounds represented by formula (I) can be obtained by bonding sialic acid to the amino terminus of the peptide chain according to condensation. These octapeptides show excellent physiological activity comparable to FTS and a half life in blood longer than that of FTS and it is expected that the affinity of the peptide to lymphocytes is also enhanced. Thus they can effectively be used as medicines for treating the lowering and abnormality of functions of the thymus.

17 Claims, No Drawings

SIALIC ACID-BONDED OCTAPEPTIDE AND PREPARATION THEREOF

BACKGROUND OF THE INVENTION

1. Field of the Invention

The present invention relates to novel sialic acid-bonded octapeptides and a method for preparing these octapeptides and more particularly to derivatives of an octapeptide similar to a serum thymic factor, FTS (Facteur Thymique Serique), effective as a drug for treating the lowering and abnormality of functions of the thymus and a method for preparing the same.

2. Description of the Prior Art

FTS which is a thymic factor is a peptide comprising 9 amino acid molecules and it has been isolated from blood by J. Bach et al. in 1976. This factor is produced in the thymus and is a physiologically active substance having an effect of inducing mature T cells by exerting an influence on T cells which pass through the thymus to promote proliferation and differentiation. This factor would be used as a medicine for treating the lowering and abnormality of functions of the thymus or the like. Thus, it has already been organochemically synthesized and its basic and clinical applications have been investigated.

However, the half life of FTS in blood is very short value of the order of several tens minutes and, therefore, a sufficient sustained effect thereof is not expected when it is administered to an organism or living body.

Under such circumstances, there has been a requirement for the development of novel compounds having physiological activity comparable to FTS and a longer half life in blood.

SUMMARY OF THE INVENTION

Accordingly, an object of the present invention is to provide a novel sialic acid-bonded octapeptide which would be effective as medicines for treating the lowering and abnormality of functions of the thymus.

Another object of the present invention is to provide a derivative of an octapeptide similar to FTS having an improved longer half life in blood and physiological activity comparable to FTS.

A further object of the present invention is to provide a method for preparing such a novel sialic acid-bonded octapeptide which would be effective as drugs for treating the lowering and abnormality of functions of the thymus.

The foregoing objects of the present invention can effectively be achieved by providing a sialic acid-bonded octapeptide represented by the following general formula (I):

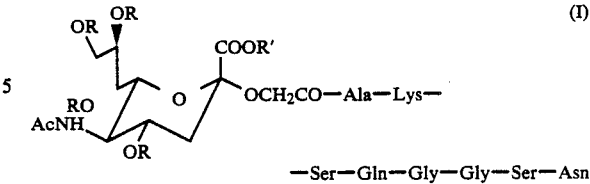

In formula (I), R represents a hydrogen atom or an acetyl group; and R' represents a lower alkyl group, an aralkyl group, a hydrogen atom or an alkali metal.

DETAILED EXPLANATION OF THE INVENTION

FTS is a physiologically active substance which can promote the maturity of T cells in the thymus and a peptide composed of 9 amino acid molecules represented by <Glu-Ala-Lys-Ser-Gln-Gly-Gly-Ser-Asn (wherein <Glu means L-pyroglutamic acid). The peptide chain of the sialic acid-bonded octapeptide is constituted by 8 amino acid molecules on the C-terminus side of FTS and the compounds represented by formula (I) are those obtained by condensing sialic acid to the amino terminus of the peptide chain.

In formula (I), R' represents a lower alkyl group, an aralkyl group, a hydrogen atom or an alkali metal atom as already defined above. Preferred examples of the lower alkyl group are those having 1 to 4 carbon atoms such as methyl, ethyl, propyl and butyl groups and most preferred is a methyl group. Examples of preferred aralkyl groups are benzyl group and phenethyl group and most preferred is a benzyl group. In addition, most preferred alkali metal atom is sodium.

Preferred examples of the sialic acid-bonded octapeptides according to the present invention include [(methyl 5-acetamido-4,7,8,9-tetra-O-acetyl-3,5-dideoxy-α-D-glycero-D-galacto-2-nonulopyranosylonato)oxyacetyl]-Ala-Lys-Ser-Gln-Gly-Gly-Ser-Asn; [(methyl 5-acetamido-3,5-dideoxy-α-D-glycero-D-galacto-2-nonulopyranosylonato)oxyacetyl]-Ala-Lys-Ser-Gln-Gly-Gly-Ser-Asn; and [(sodium 5-acetamido-3,5-dideoxy-α-D-glycero-D-galacto-2-nonulopyranosylonato)oxyacetyl]-Ala-Lys-Ser-Gln-Gly-Gly-Ser-Asn.

The novel sialic acid-bonded octapeptides of the present invention can be prepared according to a method detailed below (which is also an object of this invention):

The octapeptide derivatives of the invention represented by the following general formula (Ia):

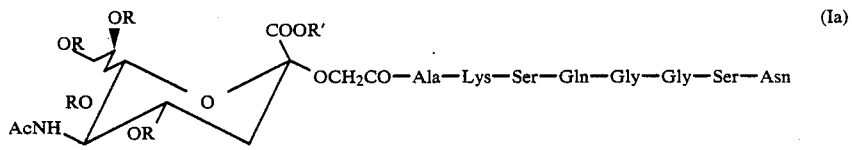

(in the formula (Ia), R represents a hydrogen atom or an acetyl group; and R' represents a lower alkyl group, an aralkyl group or a hydrogen atom) can be prepared by reacting a compound represented by the following general formula (II) with a compound represented by the following general formula (IV):

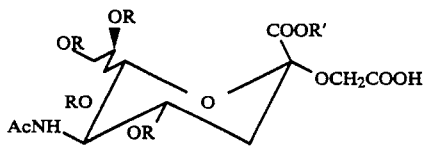

(in the formula (II), R represents a hydrogen atom or an acetyl group; and R' represents a lower alkyl group, an aralkyl group or a hydrogen atom);

$$\text{Ala-Lys}(Z_1)\text{-Ser}(Z_2)\text{-Gln-Gly-Gly-Ser}(Z_2)\text{-Asn-}Z_3 \quad (IV)$$

(wherein $Z_1$, $Z_2$ and $Z_3$ each represents a protective group), in the presence of an agent for dehydration-condensation to form a compound represented by the general formula (III):

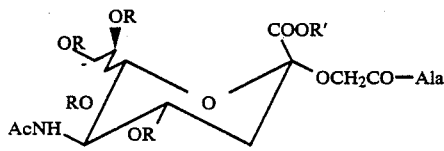

(wherein R represents a hydrogen atom or an acetyl group; R' represents a lower alkyl group, an aralkyl group or a hydrogen atom; and $Z_1$, $Z_2$ and $Z_3$ each represents a protective group) and then subjecting the compound of formula (III) to hydrogenolysis in the presence of palladium black.

The lower alkyl group represented by R' is preferably those having 1 to 4 carbon atoms such as methyl, ethyl, propyl and butyl groups and most preferred is a methyl group. Examples of preferred aralkyl groups are benzyl group and phenethyl group and most preferred is a benzyl group.

As the protective groups $Z_1$, $Z_2$ and $Z_3$, there may be used any commonly used ones and specific examples thereof include p-chlorobenzyloxycarbonyl group, t-butoxycarbonyl group and benzyloxycarbonyl group for $Z_1$; benzyl group and t-butyl group for $Z_2$; and p-nitrobenzyl ester group and t-butyl group for $Z_3$.

The reaction between the compounds represented by formulas (II) and (IV) may be performed in a proper solvent in the presence of an agent for dehydration-condensation. As the agents for dehydration-condensation there may be used those usually employed in the formation of amides and specific examples thereof are 1-ethyl-3-(3-dimethylaminopropyl)-carbodiimide (hereinafter referred to as "WSC") and dicyclohexyl carbodiimide (DCC). On the other hand, examples of solvents which may be used in the reaction include tetrahydrofuran, anhydrous dimethylformamide, a mixed solution of anhydrous acetonitrile and anhydrous dimethylformamide or a mixed solution of anhydrous methylene chloride and anhydrous dimethylformamide. A preferred solvent is anhydrous dimethylformamide.

In the foregoing method for preparing the octapeptide derivatives of the present invention, the compounds represented by formula (III) can be converted to the sialic acid-bonded octapeptides represented by the general formula (Ia) by subjecting them to hydrogenolysis in a proper solvent in the presence of palladium black. As such a solvent there may be used, for instance, water, acetic acid or a mixture thereof, preferably a mixed solvent thereof.

Moreover, the octapeptide derivatives of the present invention (those salts with alkali metal) can be prepared according to the method which comprises treating the compounds represented by formula (Ia) with an alkali to convert them to those represented by the following general formula (Ib):

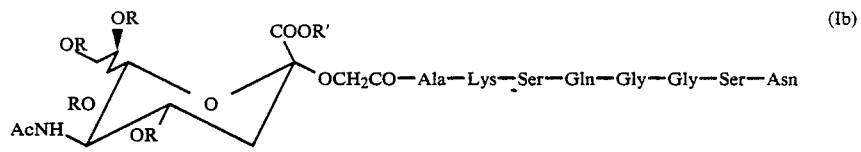

Wherein R represents a hydrogen atom or an acetyl group; and R' represents an alkali metal atom.

Examples of such alkalis usable in the reaction include sodium hydroxide, potassium hydroxide, sodium carbonate and sodium bicarbonate.

The compounds represented by the general formula (II) which can be used to form the sialic acid-bonded octapeptides of this invention can be prepared according to the following reaction processes:

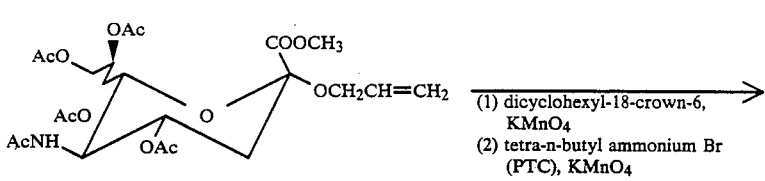

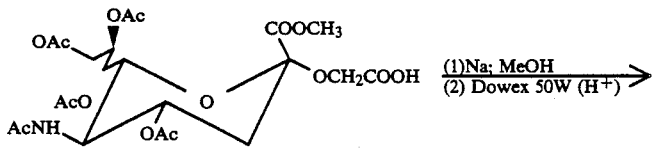

(IIa)

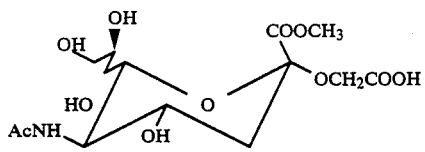

(IIb)

In addition, the compounds represented by formula (IV) can be prepared according to methods disclosed in Didier Blanot, Int. J. Peptide Protein Res., 1979, 14, pp. 41–56 and Takashi ABIKO, Chem. Pharm. Bull., 1979, 27-(9), pp. 2207–2211.

It is also possible to employ a compound: Ala-Lys($Z_1$)-Ser($Z_2$)-Gln($Z_4$)-Gly-Gly-Ser($Z_2$)-Asn-$Z_3$ instead of the compound of formula (IV) wherein $Z_1$, $Z_2$ and $Z_3$ are the same as those defined above and $Z_4$ represents a protective groul for an amino group such as 4,4'-dimethoxybenzhydryl group.

Thus, according to the present invention, novel octapeptide derivatives, i.e., sialic acid-bonded octapeptides are provided. These octapeptides show excellent physiological activity comparable to FTS and a half life in blood longer than that of FTS and it is expected that the affinity of the peptide to lymphocytes is also enhanced. Thus they can effectively be used as medicines for treating the lowering and abnormality of functions of the thymus.

The present invention will hereinafter be described in more detail with reference to the following non-limitative Examples.

EXAMPLE 1

Preparation of [(Methyl 5-acetamido-4,7,8,9-tetra-O-acetyl-3,5-dideoxy-α-D-glycero-D-galacto-2-nonulopyranosylonato)-oxyacetyl]-Ala-Lys(4-Cl-Z)-Ser(Bzl)-Gln-Gly-Gly-Ser(Bzl)-Asn-ONb (III) (wherein 4-Cl-Z is a p-chlorobenzyloxycarbonyl group; Bzl is a benzyl group; and ONb is a p-nitrobenzyloxy group)

There were dissolved 32 mg (58.2368 μmoles) of methyl (carboxymethyl 5-N-acetyl-3,5-dideoxy-4,7,8,9-tetra-O-acetyl-α-D-glycero-D-galacto-2-nonulopyranosido)-onate (II), 74 mg (58.2368 μmoles) of Ala-Lys(4-Cl-Z)-Ser(Bzl)-Gln-Gly-Gly-Ser(Bzl)-Asn-ONb.HCl, 13.4 mg (69.8842 μmoles) of WSC and 10.4 mg (58.2368 μmoles) of N-hydroxy-5-norbornene-2,3-dicarboximide (HONB) in 1 ml of anhydrous dimethylformamide followed by adding 6 mg (58.2368 μmoles) of N-methylmorpholine under ice-cooling, stirring the mixture for 2 hours and then stirring it at room temperature for additional 48 hours. The solvent was distilled off from the reaction solution under a reduced pressure, followed by adding methanol to the resulting residue, filtering off the precipitates, washing the filtered precipitates with methanol and drying them in vacuo to obtain 25 mg (yield: 23.6%) of a product in the form of powder.

Physical properties of the resultant powder are as follows:

m.p. = 195°–200° C.

TLC, Rf=0.88 [silica gel; developing solvent=n-butanol: pyridine: acetic acid: water (30:20:6:24)]

IR $\nu_{max}^{KBr}$ cm$^{-1}$: 1740 (ester)

$^1$H-NMR$_{400 MHz}$ δ ppm (DMSO-d$_6$, TMS) 1.68 (s, —NHCOCH$_3$); 1.928, 1.966, 2.003, 2.066 (all s, —OCOCH$_3$) 3.756 (s, —COOCH$_3$) 4.481 (s, Ph—CH$_2$—O—) 4,985, 5.218 (all s, Cl—Ph—CH$_2$—O—, NO$_2$—Ph—CH$_2$—O—) 7.15–8.30 (m, phenyl-H)

EXAMPLE 2

Preparation of [(Methyl 5-acetamido-3,5-dideoxy-α-D-glycero-D-galacto-2-nonulopyranosylonato)-oxyacetyl]-Ala-Lys(4-Cl-Z)-Ser(Bzl)-Gln-Gly-Gly-Ser(Bzl)-Asn-ONb (III)

There were dissolved 30 mg (78.6 μmoles) of methyl (carboxymethyl 5-N-acetyl-3,5-dideoxy-α-D-glycero-D-galacto-2-nonulopyranosido)-onate (II), 47.2 mg (37.2 μmoles) of Ala-Lys(4-Cl-Z)-Ser(Bzl)-Gln-Gly-Gly-Ser(Bzl)-Asn-ONb. HCl, 9 mg (46.9 μmoles) of WSC and 9 mg (50.2 μmoles) of HONB in 5 ml of anhydrous dimethylformamide followed by adding 3.8 mg (37.5 μmoles) of N-methylmorpholine under ice-cooling and stirring the mixture at room temperature for 60 hours. The solvent was distilled off from the reaction solution under a reduced pressure, followed by adding 5 ml of water to the resulting residue, filtering off the precipitates, washing the precipitates with water and drying them in vacuo to obtain 38 mg (yield: 74% on the basis of the octapeptide) of white powdery product.

Physical properties of the resultant white powdery product are as follows:

m.p. = 186°–190° C.

TLC, Rf=0.824 [silica gel; developing solvent=n-butanol: pyridine: acetic acid: water (30:20:6:24)]

IR $\nu_{max}^{KBr}$ cm$^{-1}$: 1740 (ester)

$^1$H-NMR$_{400 MHz}$ δ ppm (DMSO-d$_6$, TMS) 1.861 (s, —NHC OCH$_3$); 3.714 (s, —COOCH$_3$) 4.483 (s, Ph—CH$_2$—O—) 4,986, 5.218 (all s, Cl—Ph—CH$_2$—O—, NO$_2$—Ph—CH$_2$—O—) 7.21–7.45 (m, phenyl-H)

EXAMPLE 3

Preparation of [(Methyl 5-acetamido-4,7,8,9-tetra-O-acetyl-3,5-dideoxy-α-D-glycero-D-galacto-2-nonulopyranosylonato)-oxyacetyl]-Ala-Lys-Ser-Gln-Gly-Gly-Ser-Asn (Ia)

10 mg (5.6716 μmoles) of the compound obtained in Example 1 was dissolved in 3 ml of 2:1 acetic acid-water mixture and 30 mg of palladium black was added thereto to perform catalytic reduction at room temperature for 48 hours with stirring. The reaction mixture was filtered and the resultant filtrate was lyophilized to obtain 5 mg (yield=68.9%) of colorless amorphous crystals.

Physical properties of the resultant amorphous crystals are as follows:

Decomposition Point=175° C.

TLC, Rf=0.24 [silica gel; developing solvent=n-butanol: pyridine: acetic acid: water (30:20:6:24)]

$^1$H-NMR$_{400 MHz}$ δ ppm (D$_2$O, TSP) 1.966 (s, —NHC OCH$_3$); 2.100, 2.142, 2.211, 2.245 (all s, —OCOCH$_3$) 3.893 (s, —COOCH$_3$)

(As seen from the results of NMR spectroscopic analysis, all the absorbances originated from benzyl and phenyl groups were disappeared).

EXAMPLE 4

Preparation of [(Methyl 5-acetamido-3,5-dideoxy-α-D-glycero-D-galacto-2-nonulopyranosylonato)-oxyacetyl]-Ala-Lys-Ser-Gln-Gly-Gly-Ser-Asn (Ia)

Compound (III) (22 mg; 13.7 μmoles) obtained in Example 2 was dissolved in 10 ml of 2:1 acetic acid-water mixture and 60 mg of palladium black was added thereto and the resulting mixture was stirred at room temperature for 3 days to perform catalytic reduction. The reaction mixture was filtered through a Celite layer followed by lyophilizing the filtrate obtained, passing the product through a Sephadex G-25 chromatography column (developing solvent: water) to purify it and then lyophilizing the fractions obtained to recover 11.3 mg (yield=87.6%) of white powder.

Physical properties of the resultant white powdery product are as follows:

Decomposition Point=170° C.

TLC, Rf=0.133 [silica gel; developing solvent=n-butanol: pyridine: acetic acid: water (15:10:3:12)]

IR $v_{max}^{KBr}$ cm$^{-1}$: 1740 (ester)

$^1$H-NMR$_{500 MHz}$ δ ppm (D$_2$O, t-BuOH) 2.042 (s, —NHC'OCH$_3$); 3.868 (s, —COOCH$_3$)

(As seen from the results of NMR spectroscopic analysis, all the spectra derived from benzyl and phenyl groups were disappeared).

EXAMPLE 5

Preparation of [(sodium 5-acetamido-3,5-dideoxy-α-D-glycero-D-galacto-2-nonulopyranosylonato)-oxyacetyl]-Ala-Lys-Ser-Gln-Gly-Gly-Ser-Asn (Ib)

Compound (Ia) (20 mg; 21.3 μmoles) obtained in Example 4 was dissolved in a mixed solution comprising 1 ml of water and 0.16 ml of methanol, then 86 μl of 0.769N sodium hydroxide was added to the solution and the mixture was stirred at room temperature for 2 days. The reaction solution was passed through a Sephadex G-25 chromatography column (developing solvent: water) to purify it and then lyophilizing the fractions obtained to recover 18 mg (yield=89%) of white powder.

Physical properties of the resultant white powdery product are as follows:

Decomposition Point=180° C.

TLC, Rf=0.085 [silica gel; developing solvent=n-butanol: pyridine: acetic acid: water (15:10:3:12)]

IR $v_{max}^{KBr}$ cm$^{-1}$: 1600 (—COONa) 1650 (amide)

(The absorbance at 1740 cm$^{-1}$ (ester) was disappeared).

$^1$H-NMR$_{500 MHz}$ δ ppm (D$_2$O, t-BuOH)

2.040 (s, —NHC OCH$_3$);

(The signals of methyl group attached to ester group was disappeared).

What is claimed is:

1. A sialic acid-bonded octapeptide represented by the following general formula (I):

(I)

[Structure showing sialic acid derivative with OR, AcNH, COOR', OCH$_2$CO—Ala—Lys—Ser—Gln—Gly—Gly—Ser—Asn]

wherein R represents a hydrogen atom or an acetyl group; and R' represents a lower alkyl group, an aralkyl group, a hydrogen atom or an alkali metal atom.

2. A sialic acid-bonded octapeptide as set forth in claim 1 wherein the group R' represents a lower alkyl group having 1 to 4 carbon atoms, a benzyl group, a phenethyl group or an alkali metal atom.

3. A sialic acid-bonded octapeptide as set forth in claim 2 wherein the group R' is selected from the group consisting of a hydrogen atom, a methyl group, a benzyl group and a sodium atom.

4. A sialic acid-bonded octapeptide as set forth in claim 1 wherein the sialic acid-bonded octapeptide is a member selected from the group consisting of [(methyl 5-acetamido-4,7,8,9-tetra-O-acetyl-3,5-dideoxy-α-D-glycero-D-galacto-2-nonulopyranosylonato)oxyacetyl]-Ala-Lys-Ser-Gln-Gly-Gly-Ser-Asn; [(methyl 5-acetamido-3,5-dideoxy-α-D-glycero-D-galacto-2-nonulopyranosylonato)oxyacetyl]-Ala-Lys-Ser-Gln-Gly-Gly-Ser-Asn; and [(sodium 5-acetamido-3,5-dideoxy-α-D-glycero-D-galacto-2-nonulopyranosylonato)oxyacetyl]-Ala-Lys-Ser-Gln-Gly-Gly-Ser-Asn.

5. A method for preparing a sialic acid-bonded octapeptide represented by the following general formula (Ia):

(Ia)

[Structure showing sialic acid derivative with OR, AcNH, COOR', OCH$_2$CO—Ala—Lys—Ser—Gln—Gly—Gly—Ser—Asn]

wherein R represents a hydrogen atom or an acetyl group; and R' represents a lower alkyl group, an aralkyl group or a hydrogen atom;

that comprises reacting a compound represented by the following general formula (II):

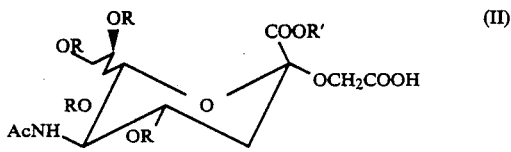

wherein R represents a hydrogen atom or an acetyl group; and R' represents a lower alkyl group, an aralkyl group or a hydrogen atom; with a compound represented by the following general formula (IV):

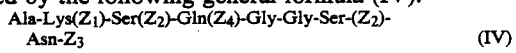

wherein $Z_1$, $Z_2$ and $Z_3$ each represent a protective group and $Z_4$ is hydrogen or a protective group; in the presence of an agent for dehydration-condensation to form a compound represented by the general formula (III):

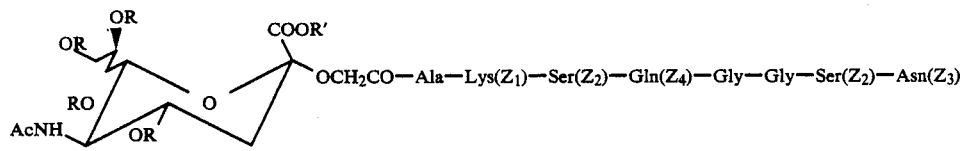

wherein R represents a hydrogen atom or an acetyl group; R' represents a lower alkyl group, an aralkyl group or a hydrogen atom; $Z_1$, $Z_2$ and $Z_3$ each represents a protective group and $Z_4$ is a hydrogen or a protective group; and then subjecting the compound of formula (III) to hydrogenolysis in the presence of an agent for catalytic reduction.

6. A method as set forth in claim 5 wherein the group R' represents a lower alkyl group having 1 to 4 carbon atoms, a benzyl group or a phenethyl group.

7. A method as set forth in claim 6 wherein the group R' is a member selected from the group consisting of a hydrogen atom, a methyl group or a benzyl group.

8. A method as set forth in claim 5 wherein the protective group $Z_1$ is a member selected from the group consisting of p-chlorobenzyloxy-carbonyl group, t-butoxy-carbonyl group and benzyloxycarbonyl group; $Z_2$ is a benzyl group or a t-butyl group; and $Z_3$ is a p-nitrobenzyl ester group or a t-butyl group.

9. A method as set forth in claim 5 wherein the agent for dehydration-condensation is a member selected from the group consisting of 1-ethyl-3-(3-dimethylaminopropyl)-carbodiimide and/or dicyclohexyl carbodiimide.

10. A method as set forth in claim 5 wherein the dehydration-condensation reaction between the compounds (II) and (IV) is carried out in the presence of a solvent.

11. A method as set forth in claim 10 wherein the solvent used in the reaction is a member selected from the group consisting of tetrahydrofuran, anhydrous dimethylformamide, a mixed solution of anhydrous acetonitrile and anhydrous dimethylformamide or a mixed solution of anhydrous methylene chloride and anhydrous dimethylformamide.

12. A method as set forth in claim 11 wherein the solvent is anhydrous dimethylformamide.

13. A method as set forth in claim 5 wherein the hydrogenolysis of the compound (III) is performed in a solvent selected from water, acetic acid or a mixture thereof.

14. A method as set forth in claim 5 wherein a compound represented by the general formula: Ala-Lys($Z_1$)-Ser($Z_2$)-Gln($Z_4$)-Gly-Gly-Ser($Z_2$)-Asn-$Z_3$ (wherein $Z_1$, $Z_2$ and $Z_3$ are the same as those defined above and $Z_4$ is a protective group) is used instead of the compound represented by the formula (IV).

15. A method as set forth in claim 14 wherein the protective group $Z_4$ is a 4,4'-dimethoxybenzhydryl group.

16. A method for preparing a sialic acid-bonded octapeptide represented by the following general formula (Ib):

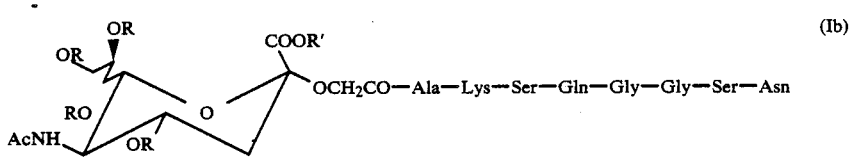

wherein R represents a hydrogen atom or an acetyl group; and R' represents an alkali metal atom which comprises hydrolyzing the compound represented by formula (Ia) defined in claim 5 with an alkali.

17. A method as set forth in claim 16 wherein the alkali usable in the reaction is selected from the group consisting of sodium hydroxide, potassium hydroxide, sodium carbonate and sodium bicarbonate.

* * * * *